(12) United States Patent
Böhme et al.

(10) Patent No.: US 11,759,105 B2
(45) Date of Patent: Sep. 19, 2023

(54) ILLUMINATING SYSTEM FOR DETERMINING THE TOPOGRAPHY OF THE CORNEA OF AN EYE

(71) Applicant: Carl Zeiss Meditec AG, Jena (DE)

(72) Inventors: Beate Böhme, Großpürschütz (DE); Rico Fuchs, Jena (DE); Günter Rudolph, Jena (DE); Michael Güntzschel, Jena (DE); Jörg Meissner, Jena (DE); Thomas Mohr, Jena (DE); Daniel Bublitz, Rausdorf (DE)

(73) Assignee: Carl Zeiss Meditec AG, Jena (DE)

( * ) Notice: Subject to any disclaimer, the term of this patent is extended or adjusted under 35 U.S.C. 154(b) by 1092 days.

(21) Appl. No.: 16/330,077

(22) PCT Filed: Aug. 31, 2017

(86) PCT No.: PCT/EP2017/071824
§ 371 (c)(1),
(2) Date: Mar. 2, 2019

(87) PCT Pub. No.: WO2018/041927
PCT Pub. Date: Mar. 8, 2018

(65) Prior Publication Data
US 2019/0223715 A1    Jul. 25, 2019

(30) Foreign Application Priority Data
Sep. 2, 2016    (DE) ............ 10 2016 216 611.5

(51) Int. Cl.
*A61B 3/107* (2006.01)
*A61B 3/00* (2006.01)
*G01B 11/25* (2006.01)

(52) U.S. Cl.
CPC ............ *A61B 3/107* (2013.01); *A61B 3/0008* (2013.01); *G01B 11/25* (2013.01)

(58) Field of Classification Search
None
See application file for complete search history.

(56) References Cited

U.S. PATENT DOCUMENTS

| | | | | |
|---|---|---|---|---|
| 2012/0147143 A1* | 6/2012 | Park | .............. | G03B 13/20 359/464 |
| 2014/0078468 A1* | 3/2014 | Bublitz | .............. | G01B 11/2513 351/212 |
| 2015/0238078 A1* | 8/2015 | Ebersbach | .............. | A61B 3/102 351/206 |

FOREIGN PATENT DOCUMENTS

| CN | 103 799976 A | 5/2014 |
|---|---|---|
| DE | 10 2011 102 3 54 A1 | 11/2012 |

(Continued)

OTHER PUBLICATIONS

K. Gourley, I. Golub, B. Chebbi, "First experimental demonstration of a Fresnel axicon," Proc. SPIE 7099, 70990D (2009).*
(Continued)

*Primary Examiner* — Michael J Hess
(74) *Attorney, Agent, or Firm* — DeWitt LLP

(57) ABSTRACT

An illumination system for producing a spatially distributed illumination pattern for measuring the cornea of an eye and, in particular, for determining the topography of the eye. In so doing, the system facilitates distance-independent measurements. The illumination system includes an illumination unit, an optical element for collimating the illumination light and a unit for producing a spatially distributed illumination pattern in the form of a fraxicon. In particular, the illumination unit includes a plurality of illumination modules which are arranged such that each illumination module illuminates part of the fraxicon, and consequently a full-area illumination is facilitated. The system for producing a spatially distributed illumination pattern serves to determine the topography of the cornea of an eye. Here, the system is (Continued)

designed as a compact module, and so it can be easily combined with other measurement systems, without interfering with the beam paths thereof.

18 Claims, 5 Drawing Sheets

(56) References Cited

FOREIGN PATENT DOCUMENTS

| DE | 10 2011 102 355 A1 | 11/2012 |
|---|---|---|
| DE | 10 2012 019 474 A1 | 4/2014 |
| EP | 2 422 691 A1 | 2/2012 |
| WO | WO 2016/203212 | 12/2016 |

OTHER PUBLICATIONS

Brahim Chebbi, Ilya Golub, Kevin Gourley, "Homogenization of on-axis intensity distribution produced by a Fresnel refractive axicon ," Optics Communications, vol. 285, Issue 7, 2012, pp. 1636-1641.*

English translation of International Report on Patentability for PCT International Search Report and Written Opinion for International Application No. PCT/EP2017/071824, dated Mar. 14, 2019, 10 pages.

Golub, "Fresnel axicon", Optics Letters, vol. 31, No. 12, Jun. 15, 2006, pp. 1890-1892.

German Search Report for Application No. 10 2016 216 611.5, dated Apr. 7, 2017, 9 pages.

International Search Report for International Application No. PCT/EP2017/071824, dated Dec. 7, 2017, 14 pages.

English translation of International Search Report for International Application No. PCT/EP2017/071824, dated Dec. 7, 2017, 3 pages.

\* cited by examiner

ILLUMINATING SYSTEM FOR DETERMINING THE TOPOGRAPHY OF THE CORNEA OF AN EYE

RELATED APPLICATIONS

This application is a National Phase entry of PCT Application No. PCT/EP2017/071824 filed Aug. 31, 2017, which application claims the benefit of priority to DE Application No. 10 2016 216 611.5, filed Sep. 2, 2016, the entire disclosures of which are incorporated herein by reference.

TECHNICAL FIELD

The invention relates to an illumination system for producing a spatially distributed illumination pattern for measuring the cornea of an eye and, in particular, for determining the topography thereof. In so doing, the solution should facilitate distance-independent measurements.

BACKGROUND

While the term keratometry should be understood to mean measuring the shape and form of the cornea of the eye, the central and peripheral radii of curvature of the cornea are measured and evaluated mathematically by specific methods within the scope of topography as a special form of keratometry.

Measuring the surface of the cornea of the human eye was found difficult because the cornea is transparent and visible light is not scattered back to any noteworthy extent.

Methods for measuring the corneal surface shape with the aid of so-called keratome-ters or keratographs has long been known according to the prior art. The concentric rings of a so-called Placido disk that are imaged onto the cornea are reflected by the tear film of the cornea and are recorded and evaluated using a camera. The reflected ring pattern detected by the camera is distorted depending on the curvature of the cornea.

The Placido disk is an illuminated disk, on which round circles are applied at regular intervals. Then, the diagnosis is on the basis of the observed reflections of the circles on the surface of the cornea, on which the circles should likewise be imaged in regular fashion.

In so doing, ideally all that should be seen now on the corneal surface is a symmetric reflection of the concentric Placido circles. By contrast, if asymmetric forms of the circles can be found, these are indications for a deviation of the corneal surface from a reference surface. Irregularities in the corneal surface can be found in the case of an astigmatism, for example, but also in the case of mechanical or chemical injuries of the cornea.

Commercially available topography systems project real Placido rings at a small distance in front of the eye onto the cornea, from where they are reflected and captured by a camera. The corneal reconstruction is based on the angular evaluation of the angle of incidence and angle of reflection of the projected Placido rings which are reflected by the cornea. Here, the deviation of the ring position on the cornea relative to the ring position of a known reference test body serves as a basis for the corneal reconstruction. A second disadvantage of such solutions can be seen in the fact that the accuracy of the measurement depends strongly on the angle relationships, and hence on the measurement distance.

Very different methods are used for determining or checking the correct measurement distance. By way of example, the measurement can be triggered automatically when the correct working distance has been reached. Firstly, this can be implemented by correcting the erroneous distance before each measurement by virtue of the distance or the position being determined with the aid of photoelectric barriers, contacts or additional measurement systems, and being corrected where necessary.

By contrast, other solutions known from the prior art are based on distance-independent measurement and a telecentric detection for determining the topography of the cornea of an eye.

DE 10 2011 102 355 A1 describes a system for topography, in which the light of a light source is collimated by use of an aspherical surface and directed onto the eye via a Fresnel axicon illuminated over the entire area thereof. Furthermore, the solution contains a light source on the optical axis and elements for output coupling the measurement radiation. In this solution, small illumination angles are produced by small deflection angles on refractive surfaces, whereas large deflection angles have to be realized by additional reflective surfaces.

A disadvantage of this solution lies in the use of reflective surfaces in the material since surface defects in this case have a substantially stronger effect on the collimation of the incident light than in the case of refractive surfaces. Furthermore, the beams extend between the light source and the collimation optical unit in divergent fashion, and so smaller free diameters are available in this installation space than between the collimation optical unit and Fresnel axicon (abbreviated fraxicon below).

Furthermore, the illumination of the fraxicon using only one light source leads to large angles of incidence occurring in the case of short focal lengths, which in turn lead to a loss of reflection in the outer zones of the Fresnel structure. Although this problem could be reme-died by increasing the focal length, this would also lead to a further reduction in the free installation space.

For the purposes of measuring the corneal curvature, the return reflections from the cornea have to be output coupled onto an imaging system in addition to the illumination. However, if the installation space is blocked by the illumination cone, output coupling can only be implemented further downstream or laterally, increasing the complexity, installation size and costs of the overall appliance.

The smaller free diameters present in the installation space also lead to a modular use of the solution, for example in conjunction with a biometric measurement arrangement, being made more difficult or even prevented as a result of possible collisions of the coaxial illumination with other beam paths.

Furthermore, it is found to be disadvantageous that the relatively large deflection angles require low manufacturing tolerances, particularly in the case of the reflective facets. Moreover, a uniform illumination can hardly be achieved.

The system described in DE 10 2011 102 354 A1 for determining the surface shape of the cornea of an eye is based on a specific Placido disk with telecentric image evaluation. The Placido disk comprises halved, toroidal elements with a semicircular cross section, which have different radii and the front, spherical or aspherical surfaces of which are directed to the cornea of the eye. The Placido disk is illuminated by way of LEDs, which are respectively arranged in the focus of the halved, toroidal elements in order to realize the projection of the rings of the Placido disk to infinity in the direction of the cornea of the eye. Although this has solved the problem of fewer free diameters by virtue of the LEDs being arranged directly on the Placido disk, the manufacture and adjustment was found to be extremely complicated and difficult.

SUMMARY OF THE INVENTION

The present invention provides an illumination system for producing a spatially distributed illumination pattern for measuring the topography of the cornea of an eye which facilitates both a distance-independent measurement and a telecentric detection. While having an installation depth that is as small as possible, the system facilitates a uniform brightness of the illumination pattern and is simple in terms of its manufacture.

According to an example embodiment, an illumination system for determining the topography of the cornea of an eye includes an illumination unit, an optical element for collimating the illumination light and a unit for producing a spatially distributed illumination pattern in the form of a fraxicon by virtue of the illumination unit consisting of a plurality of illumination modules which are arranged such that each illumination module illuminates part of the fraxicon and consequently a full-area illumination being facilitated.

The system for producing a spatially distributed illumination pattern serves to determine the topography of the cornea of an eye. Here, the system is designed as a compact module, and so it can be easily combined with other measurement systems, without colliding with the beam paths thereof.

BRIEF DESCRIPTION OF THE DRAWINGS

The invention is described in more detail below on the basis of example embodiments. For reasons of simplicity, the system for producing a spatially distributed illumination pattern for determining the topography of the cornea of an eye is abbreviated as "topography illumination" below. In the figures.

DETAILED DESCRIPTION

Figure 1:
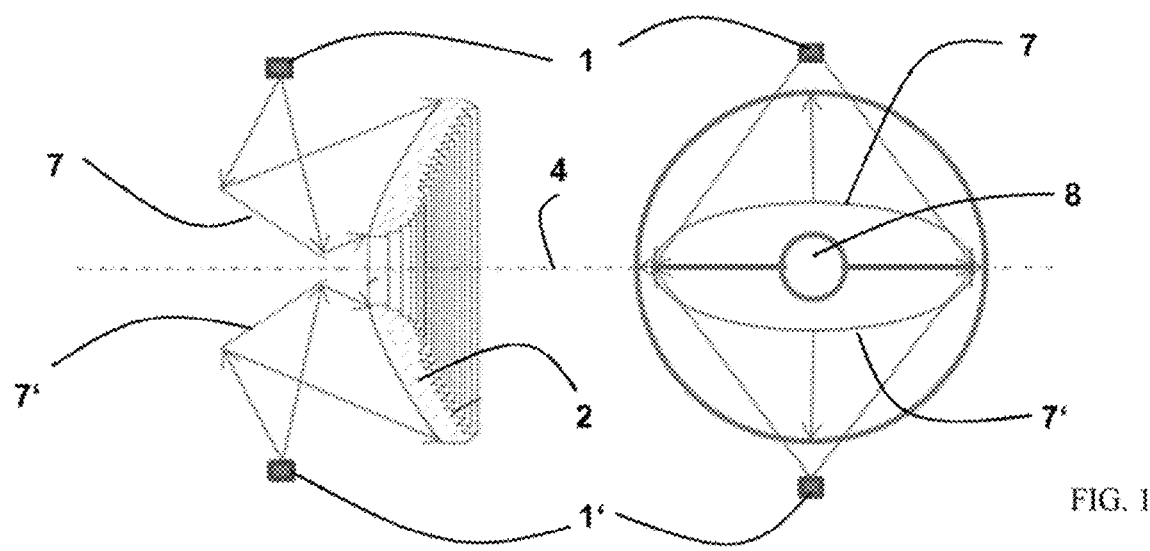
FIG. 1: depicts a topography illumination on the basis of two illumination modules, each with a plane mirror.

According to an example embodiment, an illumination system for determining the topography of the cornea of an eye includes an illumination unit, an optical element for collimating the illumination light and a unit for producing a spatially distributed illumination pattern in the form of a fraxicon.

Here, a spatially distributed illumination pattern should be understood to mean a number n of collimated individual beams, which are directed to the eye under angles of incidence that differ in terms of azimuth and radiality.

The illumination unit consists of a plurality of illumination modules which are arranged in such a way that each illumination module illuminates part of the fraxicon, and consequently a full-area illumination is facilitated.

According to example embodiments of the invention, the illumination unit includes two or more illumination modules, for example four illumination modules and in a further example six illumination modules. Here, the illumination modules are arranged in such a way that the illumination light of each illumination module illuminates part of the fraxicon.

An illumination unit with only two illumination modules has the smallest adjustment outlay since this correspondingly has the smallest number of optical elements to be aligned.

On account of their small dimensions, LEDs are increasingly used as light sources in illumination modules.

The light of the individual illumination modules is collimated on a dedicated optical partial axis in each case and directed on the part of the Fresnel axicon to be illuminated in each case.

According to first example configuration, the individual illumination modules can be arranged in such a way that the optical partial axes thereof include an angle of between 40° and 20°, for example of between 30° and 20°, with the optical axis of the system.

The proposed illumination system for determining the topography of the cornea of an eye comprises an optical element for collimating the illumination light. To this end, use is made of collimation lenses in the form of aspheres or else Fresnel lenses with aspherical power.

According to example embodiments of the invention, the collimation lenses are arranged on the optical partial axes of the illumination modules or integrated in the light sources thereof.

According to a second example configuration, the optical element for collimating the illumination light can be dispensed with if the surface of the fraxicon facing the illumination modules has a collimating effect.

The fraxicon comprises structures in which facets with different facet angles are arranged. In addition to ring-shaped or mesh-like structures, other structures are also conceiv-able.

According to example embodiments of the invention, one or more reflective optical elements, such as plane mirrors, concave mirrors or else faceted concave mirrors, are used in the illumination modules.

According to a third example configuration, facets are only present on the cornea-facing surface of the fraxicon, wherein the facet angles are designed in such a way that the spatially distributed illumination pattern is only produced by refraction of the illumination light.

However, this is only the case if the optical partial axes of the illumination modules form an angle in relation to the optical axis of the system.

According to a fourth example configuration, the illumination modules arranged at an angle to the optical axis of the system comprise separate, appropriately adapted and aligned fraxicons.

Here, too, the facet angles can be designed in such a way that the spatially distributed illumination pattern is produced only by refraction of the illumination light.

In an example embodiment, the fraxicon(s) is/are able to be manufactured as an injection molded part.

According to a further example configuration, an illumination module including a light source, the optionally present reflective optical elements, an optionally present optical element for collimating the illumination light and a separate fraxicon can be manufactured as a unit.

Below, different variants of the invention are explained in more detail on the basis of graphical illustrations, wherein the employed fraxicon has ring-shaped structures.

To this end, FIG. 1 depicts a topography illumination on the basis of two illumination modules, each with a plane mirror.

What can be gathered from the left image is that the illumination light of the illumination source 1 and 1' is directed onto the fraxicon 2 via the plane mirrors 7 and 7'. Along the further beam path (not illustrated), the illumination light is refracted at the facets thereof, a spatially distributed illumination pattern is produced and said spatially distributed illumination pattern is imaged on the eye (not illustrated). The optical axis of the topography illumination is denoted by 4.

What can be gathered from the right image is that the plane mirrors 7 and 7' each have a cutout for a telecentric detection beam path 8.

In this solution, the edges of the plane mirrors contacting at the bend cannot be infi-nitely small, which is why a loss of intensity is to be expected at this contacting edge. However, the following different configuration variants emerge herefrom.

Figure 2:
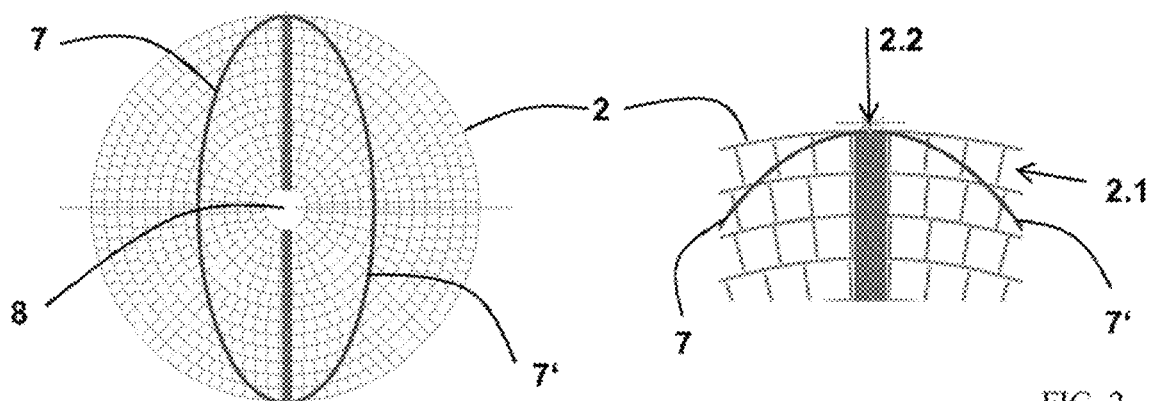
FIG. 2: depicts a first configuration of the solution according to FIG. 1, FIG. 3: depicts a second configuration of the solution according to FIG. 1, FIG. 4: depicts a topography illumination on the basis of four illumination modules, each with a plane mirror.

According to a first configuration of this illumination variant, illustrated in FIG. 2, the contacting edge of the plane mirrors 7 and 7' is placed directly on a facet zone 2.2, and so an entire radial component is not illuminated along this zone. Here, a facet zone 2.2 is a part of the ring-shaped facets 2.1 with different radii. The consequently "omitted" measurement points can be interpolated relatively well by the surrounding, illuminated measurement points.

Figure 3:
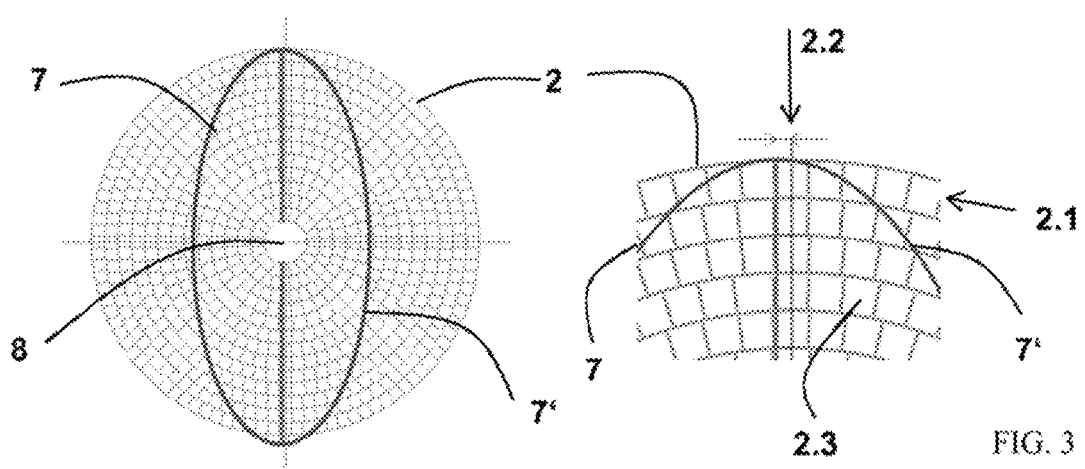

In the configuration of this illumination variant illustrated in FIG. 3, the contacting edge of the plane mirrors 7 and 7' is positioned directly on a common edge of the facet zones 2.2. For this, the contacting edge of the plane mirrors 7 and 7' has to be extremely narrow on the one hand. On the other hand, the design of the fraxicon 2 must be configured in such a way that the number of facets 2.3 per ring is a multiple of 2 because there is no common (continuous) edge otherwise. All measurement points are illuminated in this variant, and so an interpolation becomes superfluous.

Figure 4:
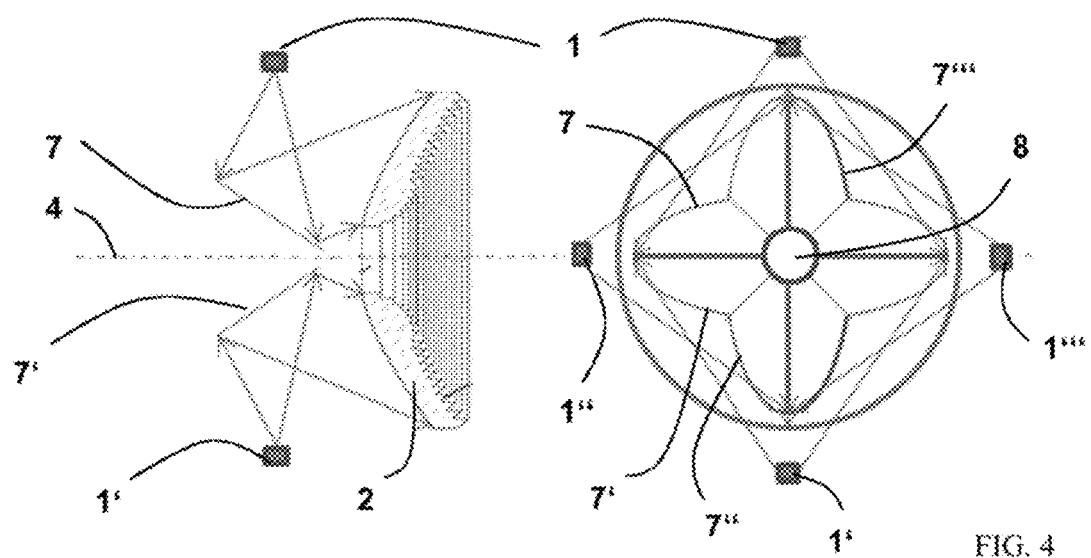

FIG. 4 shows a topography illumination on the basis of four illumination modules, each with a plane mirror.

While the left image is identical to FIG. 1, it is possible to gather from the right image that plane mirrors 7 to 7''' each have a cutout for a telecentric detection beam path 8. This solution also has the problem of the possible loss of intensity at the contacting edges of the plane mirrors. Here, too, the "omitted" measurement points can be interpolated relatively well (in a manner analogous to FIG. 3) by the surrounding, illuminated measurement points.

Figure 5:
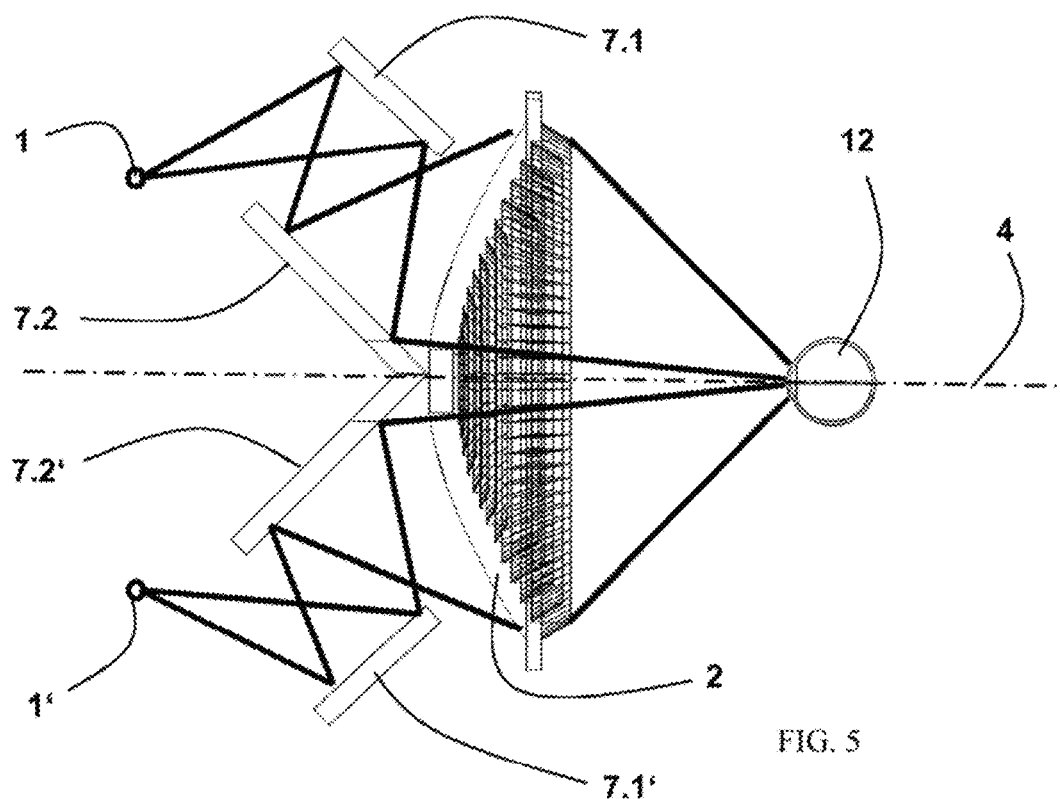
FIG. 5: depicts a topography illumination on the basis of two illumination modules, each with two plane mirrors.

FIG. 5 shows a topography illumination on the basis of two illumination modules, each with two plane mirrors. Here, the illumination light of the illumination source 1 and 1' is directed onto a fraxicon 2 via two plane mirrors 7.1 and 7.2 or 7.1' and 7.2' in each case. Along the further beam path, the illumination light is collimated on the back side of the fraxicon 2, said illumination light is refracted at the facets of the latter, a spatially distributed illumination pattern is produced and said spatially distributed illumination pattern is imaged on the eye 12.

What can be gathered from FIG. 5 is that the contacting edge of the plane mirrors 7.2 and 7.2' is not situated on the optical axis. This ensures that the contacting edge is positioned directly on a common edge of the facet zones according to the solution described in FIG. 3 and, consequently, a complete, spatially distributed illumination pattern is produced.

For a possible configuration of the solution according to FIG. 5, each of the two illumination modules is based on an illumination source in the form of an LED and two plane mirrors. The employed fraxicon has the following dimensions:

Focal length of the collimation lens: f=140 mm
Diameter of the axicon: d=142 mm
Angle of the mirrors 2 in relation to the optical axis: 45°
Angle between mirror 2 and mirror 1: 2.5°

As a result, the illumination unit has an installation length of 76 mm with an overall width of 188 mm. The illumination unit can be produced from both plastic and glass.

Figure 6:
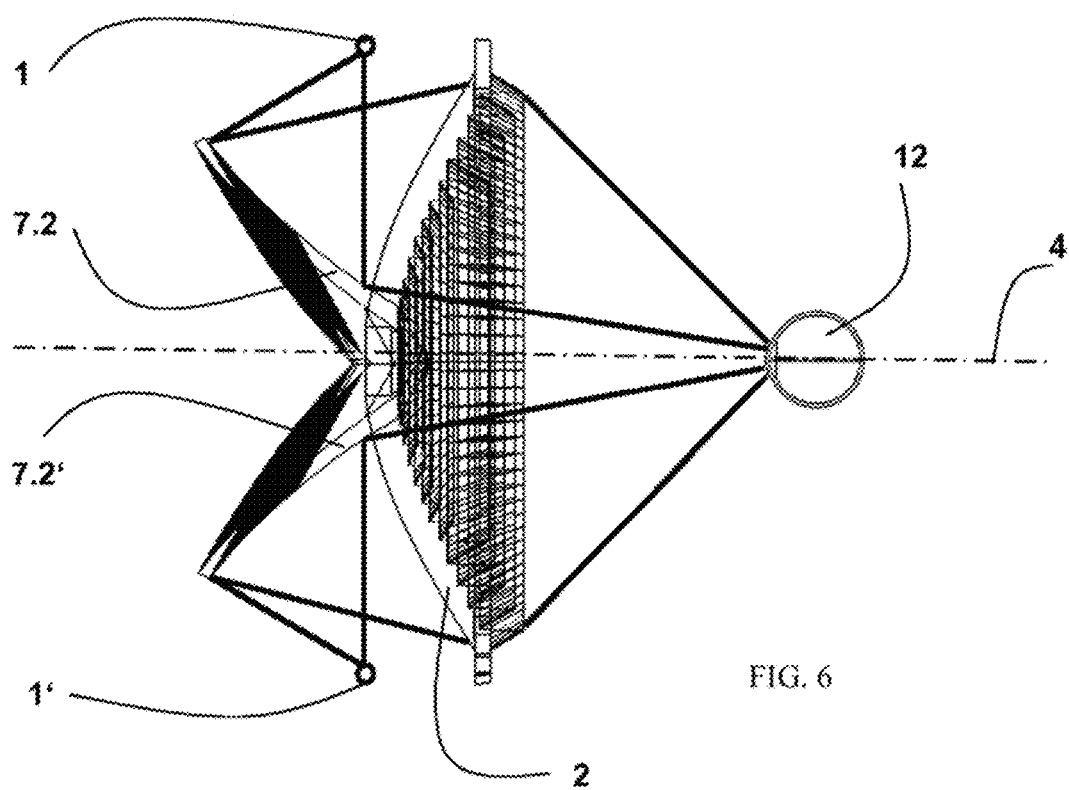
FIG. 6: depicts a topography illumination on the basis of two illumination modules, each with a concave mirror.

FIG. 6 shows a topography illumination on the basis of two illumination modules, each with a concave mirror. Here, the illumination light of the illumination sources 1 and 1' is directed onto the fraxicon 2 via the concave mirrors 11 and 11'. Along the further beam path, the illumination light is collimated on the back side of the fraxicon, said illumination light is refracted at the facets of the latter, a spatially distributed illumination pattern is produced and said spatially distributed illumination pattern is imaged on the eye 12.

For a possible configuration of the solution according to FIG. 6, each of the two illumination modules is likewise based on an illumination source 1 in the form of an LED with a collimation lens (not illustrated) arranged in front of it. In this case, with the following dimensions:

For a possible configuration of the solution according to FIG. 6, each of the two illumination modules is based on an illumination source in the form of an LED and a concave mirror. The employed fraxicon has the following dimensions:

Nominal focal length the collimation lens: f=140 mm
Diameter of the axicon: d=142 mm In this solution, the focal length can be reduced to 73 mm by way of the employed concave mirror.

The illumination unit, having an overall width of 142 mm, only has an installation length of 40 mm and fewer optical elements. However, the production of the concave mirrors is complicated and hence only expedient when using moldable plastic.

In the variants with two illumination modules, illustrated in FIGS. 5 and 6, the illumination is implemented centrally, i.e., along the optical axis of the fraxicon. However, according to a further example configuration, it is also possible to illuminate the fraxicon in lateral fashion, i.e., at a tilt to the optical axis of the illumination system. In principle, this is possible in all variants described previously and also in the variants described below. However, it is necessary, to this end, to appropriately adapt the fraxicon, i.e., the back side thereof with collimating effect, and also the facets on the front side thereof.

Figure 7:
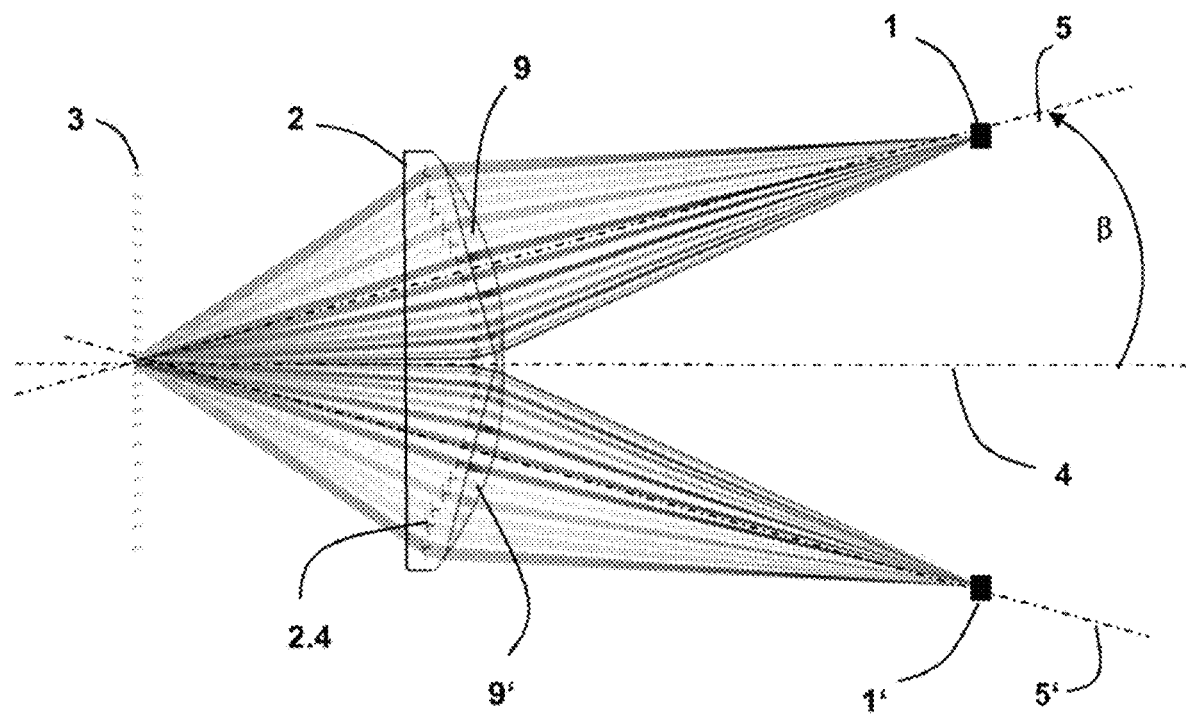
FIG. 7: depicts a topography illumination on the basis of four illumination modules in a side view and from the view of the eye.

FIG. 7 shows a topography illumination on the basis of four illumination modules in a side view.

What can be gathered from the side view (left image) is that the illumination light of the illumination sources 1 and 1' is directed to a fraxicon 2, the back side (facing the illumination light sources) of which is embodied as collimation lenses 9 and 9'. Along the further beam path, the illumination light is refracted at the facets 2.4 thereof, a spatially distributed illumination pattern is produced and said spatially distributed illumination pattern is imaged on the eye situated in the plane 3. The optical axis of the topography illumination is denoted by 4; the optical partial axes of the individual illumination modules are denoted by 5 and 5'.

The optical partial axes 5 and 5' of the individual illumination modules 1 and 1' form an angle β of, for example, between 40° and 20°, in another example, of between 30° and 20°, in relation to the optical axis 4 of the system.

A substantial reduction in the installation depth can already be achieved by these solution variants. While an individual illumination unit (known from the prior art) must illuminate an angle range of approximately +/−38° for the full-area illumination of the unit for the purposes of producing a spatially distributed, distance-independent illumination pattern, this angle range for the illumination of a segment-shaped part of the unit for producing a spatially distributed, distance-independent illumination pattern is only approximately +/−10°. The focal length could now be reduced, optionally up to an angle range of approximately +/−38°, which would lead to substantial shortening of the installation length of the individual illumination modules.

According to example embodiments of the invention, a further reduction in the installation depth is achieved by virtue of the individual illumination modules comprising lenses and/or mirrors in addition to a light source in order to facilitate a full-area illumination of the parts of the Fresnel axicon.

Although a more uniform illumination likewise already emerges from the division of the illumination unit into a plurality of illumination modules and the reduction of the area to be illuminated by an illumination source connected therewith, the use of lenses and/or mirrors can, however, improve this even further.

Below, different variants of the invention are explained in more detail on the basis of graphical illustrations, in which the Fresnel axicon is merely illustrated as a box.

For a better understanding, reference is made to the solution according to DE 10 2011 102 355 A1, in which the eye is detected coaxially to the vertex of the eye through a central opening in the Fresnel axicon. Only the different illumination variants will be discussed below.

Figure 8:
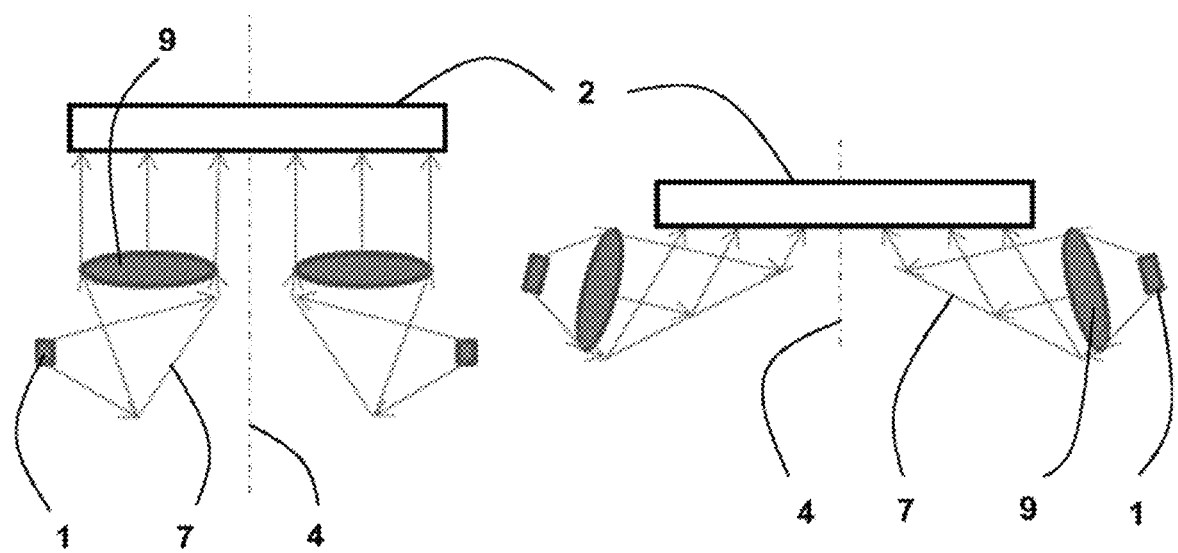
FIG. 8: depicts a topography illumination on the basis of two illumination modules, each with a collimation lens and a plane mirror.

FIG. 8 shows a topography illumination on the basis of two illumination modules, each with a collimation lens and a plane mirror.

In the left image, the illumination light of the illumination sources 1 and 1' is directed onto the fraxicon 2 via the plane mirrors 7 and 7' and the collimation lenses 9 and 9'. In this variant, the illumination is implemented centrally, i.e., along the optical axis 4 of the fraxicon 2.

In contrast to the left image, the illumination light of the illumination sources 1 and 1' in the right image is directed onto the fraxicon 2 via, firstly, the collimation lenses 9 and 9' and then the plane mirrors 7 and 7'. Here, the fraxicon 2 is illuminated at a tilt to the optical axis 4 thereof. As already mentioned, this requires the facets of the fraxicon to be adapted accordingly to the tilted illumination.

Figure 9:
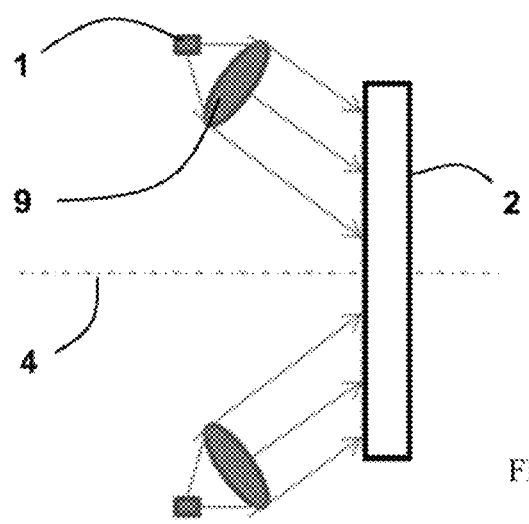
FIG. 9: depicts a topography illumination on the basis of two illumination modules, each with a collimation lens only.

FIG. 9 shows a topography illumination on the basis of two illumination modules, each with a collimation lens. In this variant, the illumination modules are aligned in such a way that mirrors can be dispensed with. The illumination light of the illumination sources 1 and 1' is directed onto the fraxicon 2 via the collimation lenses 9 and 9'.

Figure 10:
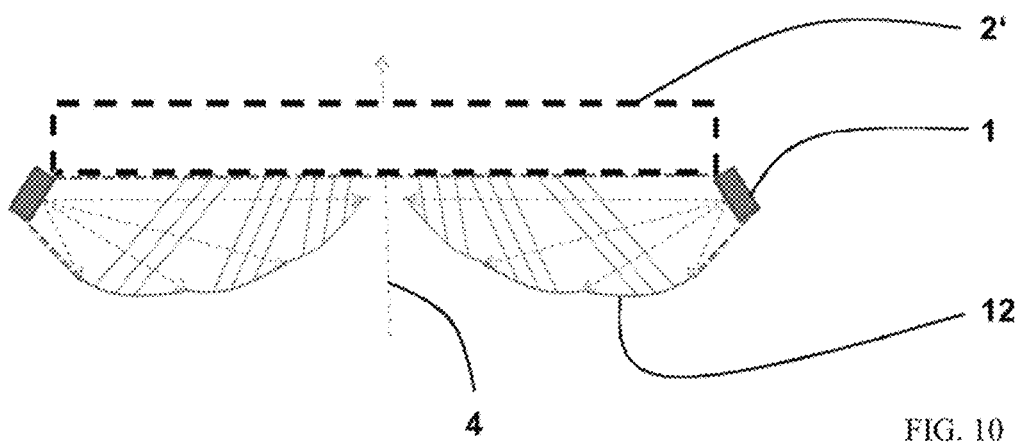
FIG. 10: depicts a topography illumination on the basis of two illumination modules, each with a faceted concave mirror.

FIG. 10 shows a topography illumination on the basis of two illumination modules, each with a faceted concave mirror. In contrast to FIG. 9, use is made here of two faceted concave mirrors 12 and 12', which adopt both the deflection of the illumination light and the collimation thereof. Consequently, the fraxicon 2 (illustrated using dashed lines) can be dispensed with in this embodiment variant.

Figure 11:
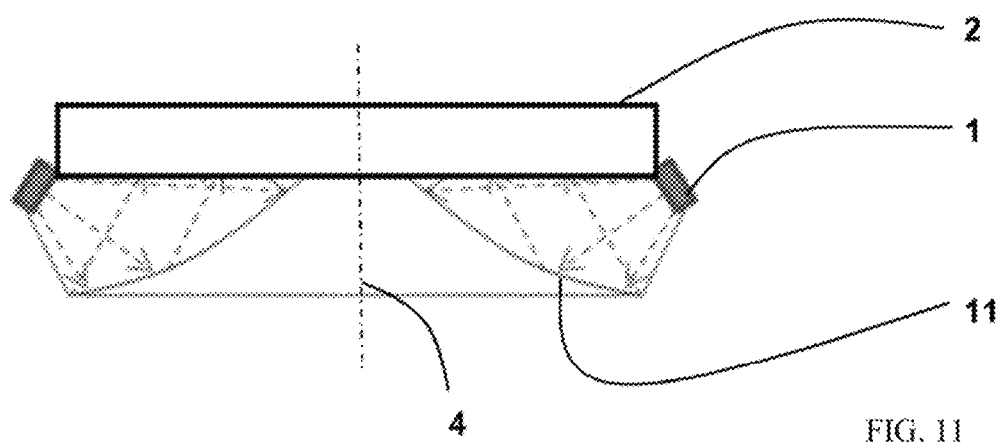
FIG. 11: depicts a topography illumination, in which the side of the fraxicon facing the illumination source is embodied as a simple concave mirror.

A further example configuration is illustrated in FIG. 11. In the topography illumination shown here, the back side, i.e., the side of the fraxicon 2 facing the illumination sources 1 and 1', is embodied as a concave mirror 11. By way of example, this is possible if the fraxicon 2 is manufactured from plastics. In principle, it is also possible for the concave mirrors to be embodied as faceted concave mirrors. If use is made of faceted concave mirrors, these can for example adopt the collimation and/or at least some of the effects of the fraxicon 2.

These two variants are advantageous in that the installation depth of the overall arrangement can be reduced as a result of the lateral illumination.

Even though the above-described variants of the topography illumination according to the invention always only exhibit two illumination modules, a plurality of illumination modules may, in principle, also be present. Furthermore, the individual illumination modules may also contain more than one mirror and/or more than only one collimation lenses. In particular, the collimation lenses can be embodied not only as aspheres but also as Fresnel lenses with an aspherical power.

The use of Fresnel lenses (with a collimating effect) are particularly advantageous to the effect that the weight of the overall structure, consisting of a Fresnel lens and a fraxicon, is substantially reduced.

Both the division of the illumination unit into a plurality of illumination modules and the use of mirror elements for deflecting (bending) the individual illumination beam paths leads to a reduction in the installation length of the topography illumination, as a result of which space is also cleared for beam paths of other ophthalmological units. The division of the illumination radiation into a plurality of separate illumination beam paths further leads to the angles of incidence of the illumination on the fraxicon becoming smaller.

This reduces the problem of the reduction in intensity as a result of reflected stray light components. However, conversely, this also means that the distance of the illumination sources of the illumination modules from the fraxicon can be reduced. This can additionally contribute to the reduction in the installation space.

The solution according to the invention provides a system for producing a spatially distributed illumination pattern for measuring the topography of the cornea of an eye which facilitates both a distance-independent measurement and a telecentric detection. The system has a small installation depth and ensures a uniform brightness of the illumination pattern.

The installation depth can be substantially reduced by dividing the illumination unit into a plurality of illumination modules. Moreover, smaller angles of incidence arise for the illumination beams, as a result of which power losses in the edge regions of the unit for producing a spatially distributed illumination pattern are avoided. In the case of a fraxicon, the spatially distributed illumination pattern can now be produced exclusively by refraction.

Consequently, it is possible to dispense with the production of the refractively effec-tive surfaces that are more sensitive to tolerances in any case, as a result of which the stray light necessarily arising at these surfaces is reduced.

Smaller angles likewise arise for the facets of the Fresnel axicon as a result of the smaller angles of incidence, as a result of which the manufacture, in particular as an injection molded part, is substantially simplified.

The distribution of the illumination unit into a plurality of illumination modules further leads to the focal length of the illumination modules being able to be reduced, and so the installation depth can be further reduced.

Furthermore, the following advantages are connected to example embodiments of the system according to the invention for producing a spatially distributed illumination pattern for measuring the topography of the cornea of an eye:

Installation space is kept free for the telecentric imaging of the light reflected at the cornea and further system components in the optical axis.

So-called Fresnel losses for large illumination angles are avoided.

Manufacturing costs are reduced by only using refractive surfaces.

The manufacture as an injection molded part is facilitated by reducing thickness dif-ferences as a consequence of smaller dimensions.

Optical elements for separating or superimposing illumination and measurement beam paths are dispensed with.

The invention claimed is:

1. An illumination system for determining the topography of the cornea of an eye, comprising:
    an illumination unit;
    a collimating optical element that collimates illumination light emitted by the illumination unit; and
    a unit that produces a spatially distributed illumination pattern in the form of a first fraxicon;
    wherein the illumination unit comprises a plurality of illumination modules arranged such that each of the plurality of illumination modules illuminates a part of the first fraxicon and a first number of the illumination modules is equal to a second number of the parts of the fraxicon illuminated by the plurality of the illumination modules and each of the parts illuminated encompasses a fraction of the fraxicon based on the second number of parts and consequently a full-area illumination of the cornea of the eye is facilitated.

2. The illumination system as claimed in claim 1, wherein the illumination unit comprises two or more illumination modules.

3. The illumination system as claimed in claim 1, wherein the illumination unit comprises four illumination modules.

4. The illumination system as claimed in claim 1, wherein the illumination unit comprises six illumination modules.

5. The illumination system as claimed in claim 1, wherein individual illumination modules of the plurality of illumination modules are arranged in such a way that optical partial axes thereof include an angle of between 40° and 20° with the optical axis of the first fraxicon.

6. The illumination system as claimed in claim 5, wherein individual illumination modules of the plurality of illumination modules are arranged in such a way that optical partial axes thereof include an angle of between 30° and 20° with the optical axis of the first fraxicon.

7. The illumination system as claimed in claim 1, further comprising collimation lenses that collimate the illumination light, said collimation lenses being arranged on the optical partial axes of the illumination modules or being integrated in the light sources thereof.

8. The illumination system as claimed in claim 1, the first fraxicon further comprising a surface of the first fraxicon facing the illumination modules that has a collimating effect.

9. The illumination system as claimed in claim 1, wherein the illumination modules further comprise one or more reflective optical elements.

10. The illumination system as claimed in claim 9, wherein the reflective optical elements are selected from a group consisting of plane mirrors, concave mirrors and faceted concave mirrors.

11. The illumination system as claimed in claim 1, wherein the illumination unit, comprises two illumination modules each including two plane mirrors in addition to a light source.

12. The illumination system as claimed in claim 1, wherein the illumination unit, comprises two illumination modules each including a faceted concave mirror in addition to a light source.

13. The illumination system as claimed in claim 1, wherein the illumination modules are arranged at an angle to an optical axis of the system and comprising a second fraxicon,
    each of the illumination modules being appropriately adapted and aligned with one of the first and second fraxicons.

14. The illumination system as claimed in claim 1, wherein a side of the first fraxicon facing the illumination modules comprises a concave mirror.

15. The illumination system as claimed in claim 1, wherein the first fraxicon comprises an injection molded part.

16. The illumination system as claimed in claim 14, wherein the first fraxicon comprise an injection molded part.

17. The illumination system as claimed in claim 1, wherein the illumination module comprising a light source, optionally present reflective optical elements, an optionally present optical element for collimating the illumination light and the separate first fraxicon is manufactured as a unit.

18. The illumination system as claimed in claim 14, wherein the illumination module comprising a light source, optionally present reflective optical elements, an optionally present optical element for collimating the illumination light and the separate first fraxicon is manufactured as a unit.

* * * * *

UNITED STATES PATENT AND TRADEMARK OFFICE
CERTIFICATE OF CORRECTION

| | |
|---|---|
| PATENT NO. | : 11,759,105 B2 |
| APPLICATION NO. | : 16/330077 |
| DATED | : September 19, 2023 |
| INVENTOR(S) | : Beate Böhme et al. |

It is certified that error appears in the above-identified patent and that said Letters Patent is hereby corrected as shown below:

On the Title Page

On Page 2, in Item (56), under "Other Publications", in Column 2, Line 3, delete "axicon ," and insert --axicon,--

In the Specification

Column 1, Line 33, delete "keratome-ters" and insert --keratometers--

Column 2, Line 35, delete "reme-died" and insert --remedied--

Column 4, Line 51, delete "conceiv-able." and insert --conceivable.--

Column 5, Line 30, delete "infi-nitely" and insert --infinitely--

Column 9, Line 2, delete "effect-tive" and insert --effective--

Signed and Sealed this
Twelfth Day of December, 2023

Katherine Kelly Vidal
*Director of the United States Patent and Trademark Office*